(12) United States Patent
De La Poterie

(10) Patent No.: US 7,358,303 B2
(45) Date of Patent: *Apr. 15, 2008

(54) COMPOSITION COMPRISING AT LEAST ONE FIRST SEMI-CRYSTALLINE POLYMER AND AT LEAST ONE SECOND FILM-FORMING POLYMER

(75) Inventor: Valérie De La Poterie, Le Chatelet en Brie (FR)

(73) Assignee: L'Oréal, S.A., Paris (FR)

( * ) Notice: Subject to any disclaimer, the term of this patent is extended or adjusted under 35 U.S.C. 154(b) by 10 days.

This patent is subject to a terminal disclaimer.

(21) Appl. No.: 11/119,924

(22) Filed: May 3, 2005

(65) Prior Publication Data

US 2005/0201958 A1    Sep. 15, 2005

Related U.S. Application Data

(63) Continuation of application No. 10/138,325, filed on May 6, 2002, now Pat. No. 6,946,518.

(30) Foreign Application Priority Data

May 4, 2001 (FR) .................................. 01 06042

(51) Int. Cl.
| A61K 8/96 | (2006.01) |
| A61K 8/81 | (2006.01) |
| A61K 8/85 | (2006.01) |
| A61K 8/90 | (2006.01) |
| A91K 8/91 | (2006.01) |

(52) U.S. Cl. ........................... 525/50; 525/55; 525/63; 525/70; 525/88; 525/451

(58) Field of Classification Search .................. 525/50, 525/55, 63, 70, 88, 451
See application file for complete search history.

(56) References Cited

U.S. PATENT DOCUMENTS

| 4,423,031 | A |   | 12/1983 | Murui et al. |
| 5,156,911 | A |   | 10/1992 | Stewart |
| 5,302,380 | A | * | 4/1994  | Castrogiovanni et al. ..... 424/63 |
| 5,519,063 | A |   | 5/1996  | Mondet et al. |
| 5,736,125 | A | * | 4/1998  | Morawsky et al. ........... 424/59 |
| 5,874,072 | A |   | 2/1999  | Alwattari et al. |
| 5,985,258 | A |   | 11/1999 | Alwattari et al. |
| 6,180,123 | B1 |  | 1/2001  | Mondet |

2003/0064038 A1    4/2003    Auguste et al.

FOREIGN PATENT DOCUMENTS

| EP | 0 367 015 | 5/1990 |
| EP | 0 550 745 | 7/1993 |
| EP | 0 847 753 | 6/1998 |
| EP | 0 951 897 | 10/1999 |
| EP | 1 010 418 | 6/2000 |
| EP | 1 163 896 | 12/2001 |
| EP | 1 281 385 | 2/2003 |
| FR | 2 262 303 | 9/1975 |
| JP | 2000-219618 | 8/2000 |
| WO | WO 92/07913 | 5/1992 |
| WO | WO 95/15741 | 6/1995 |
| WO | WO 96/33690 | 10/1996 |
| WO | WO 96/36308 | 11/1996 |
| WO | WO 01/19333 | 3/2001 |
| WO | WO 200119333 A1 * | 3/2001 |

OTHER PUBLICATIONS

English language Derwent Abstract of EP 0 847 753, Jun. 17, 1998.
English language Derwent Abstract of EP 1 010 418, Jun. 21, 2000.
English language Derwent Abstract of EP 1 163 896, Dec. 19, 2001.
English language Derwent Abstract of FR 2 262 303, Sep. 19, 1975.
Patent Abstract of Japan, Publication No. 2000-219618, Jan. 28, 1999.
Shunichi Nojima et al., "Melting Behavior of Poly($\epsilon$-caprolactone)-block-Polybutadiena Copolymers," Macromolecules, vol. 32, No. 11, Jun. 1, 1999, pp. 3727-3734.
B. Boutevin et al., "Study of morphological and mechanical properties of PP/PBT blends," Polymer Bulletin, vol. 34, No. 1, Jan. 1995, pp. 117-123.
Pratima Rangarajan et al., "Morphology of Semicrystalline Block Copolymers of Tehylene-(Ethylene-alt-propylene)," Macromolecules, vol. 26, No. 17, Aug. 16, 1993, pp. 4640-4645.
D. Richter et al., "Polymer Aggregates with Crystalline Cores: The System Polyethylene-Poly(ethylenepropylene)," Macromolecules, vol. 30, No. 4, Feb. 24, 1997, pp. 1053-1058.
I.W. Hamley, "Crystallizationi in Block Copolymers," Advances in Polymer Science, vol. 148, 1999, pp. 113-137.

* cited by examiner

*Primary Examiner*—Kelechi C. Egwim
(74) *Attorney, Agent, or Firm*—Finnegan, Henderson, Farabow, Garrett & Dunner, LLP

(57) ABSTRACT

The invention relates to a composition comprising, in a physiologically acceptable medium, at least one first semi-crystalline polymer having a melting point of greater than or equal to 30° C., and at least one second film-forming polymer capable of forming a hydrophobic film at room temperature. The composition makes it possible to obtain a film that is more resistant to removal by cold water than to removal by warm water. The composition can be applied to the making up and care of keratin materials.

41 Claims, No Drawings

COMPOSITION COMPRISING AT LEAST ONE FIRST SEMI-CRYSTALLINE POLYMER AND AT LEAST ONE SECOND FILM-FORMING POLYMER

This is a continuation of application Ser. No. 10/138,325, filed May 6, 2002, now U.S. Pat. No. 6,946,518 which claims priority under 35 U.S.C. § 119 to French Patent Application No. 01 06042, filed May 4, 2001, both of which are incorporated herein by reference.

The present invention relates to a cosmetic composition comprising at least one semi-crystalline polymer and a polymer capable of forming a hydrophobic film, which can be used as a makeup or care composition for a keratin material such as the skin, the eyelashes, the eyebrows, the hair and the nails, of human beings. The invention also relates to a cosmetic makeup or care process for a keratin material.

The composition may be in the form of a mascara, an eyeliner, a product for the lips, a face powder, an eyeshadow, a foundation, a makeup product for the body, a concealer product, a product for the nails, an antisun composition, a skin coloring composition or a skincare product. For example, the invention relates to a mascara.

Mascara compositions in the form of a wax-in-water emulsion comprising surfactants are known from WO-A-95/15741. However, the makeup film obtained with these compositions does not always show good water resistance, and when the film comes into contact with water, for example when bathing or taking a shower, it can partially disintegrate by being worn away or by spreading around the eyes. The wearing away of the film gives rise to a substantial reduction in the intensity of the color of the makeup, thus obliging the consumer to freshen the application of the mascara. As regards the spreading of the film, this forms a very unsightly aureole around the area to which makeup has been applied. Tears and perspiration also cause these same drawbacks.

To promote the water resistance of makeup, it is known practice from U.S. Pat. No. 4,423,031 to use acrylic polymers in aqueous dispersion. However, the mascara may be difficult to remove and may require the use of special makeup removers based on oils or on organic solvents. Such makeup removers may irritate the eyes, they may in particular cause stinging or they may leave a veil over the eyes, or alternatively they may leave an uncomfortable greasy residual film on the skin around the eyes (eyelids).

To avoid the use of these special makeup removers, it is possible to use soap and water, as disclosed in WO-A-96/33690, by proposing a mascara comprising a water-insoluble polymer and a water-soluble film-forming polymer. However, the use of soap may cause eye discomfort due to stinging or to the deposition of a veil over the eyes. Soap also dissolves the film of makeup, which then spreads around the eyes and forms unsightly aureoles and stains the skin.

The use of warm water, for example water with a temperature above or equal to 35° C. (temperature measured at atmospheric pressure), such as ranging from about 35° C. to 50° C., makes it possible to avoid at least one of the drawbacks of the makeup removers known, but the cold-water-resistant mascara compositions described previously cannot be removed with warm water.

An aspect of the present invention is a cosmetic composition that can be removed with warm water while at the same time having improved cold-water resistance.

The inventor has discovered that such a composition may be obtained using at least one film-forming polymer capable of forming a hydrophobic film and at least one specific semi-crystalline polymer. After applying the composition to a keratin material, such as the eyelashes, the makeup obtained shows improved resistance to removal by cold water, that is to say to water with a temperature below or equal to 30° C., for example when bathing, and/or to tears and/or to perspiration, compared to resistance to removal in the presence of warm water. The makeup is thus more easily removed with warm water, such as by rubbing with cotton wool or gauze: the makeup detaches easily from the eyelashes and can be removed from the eyelashes without fragmenting (in the form of a sheath) or in the form of fragments or pieces. The makeup thus removed does not spread on the skin, which avoids the formation of aureoles around the eyes; the skin is not stained when removing the makeup and remains clean. The makeup is removed more simply with warm water, including warm water containing no detergent such as soaps. For the makeup removal, the warm water used may be tap water, demineralized water or mineral water brought to a temperature of greater than or equal to 35° C., for example, from about 35° C. to 50° C.

According to one aspect of the invention, there is provided a composition comprising, in a physiologically acceptable medium, at least one first semi-crystalline polymer with a melting point of greater than or equal to 30° C., and at least one second film-forming polymer capable of forming a hydrophobic film at room temperature.

Another aspect of the invention is the use of a composition as defined above to obtain a film applied to a keratin material, the film being resistant to cold water and/or removable with warm water.

A further aspect of the invention is a cosmetic makeup or care process for a keratin material, comprising the application of a composition as defined above to the keratin material.

Yet another aspect of the invention is the use of a first semi-crystalline polymer with a melting point of greater than or equal to 30° C., and at least one second film-forming polymer capable of forming a hydrophobic film at room temperature, in a cosmetic makeup or care composition for a keratin material, to obtain a film applied to the keratin material that is resistant to cold water and/or that can be removed with warm water.

Another aspect of the invention is also a cosmetic process for removing makeup from a keratin material made up with a composition as defined above, comprising rinsing the said made-up keratin material at least once with warm water maintained at a temperature of greater than or equal to 35° C.

One aspect of the invention is a composition comprising, in a physiologically acceptable medium, at least one first semi-crystalline polymer having a melting point of greater than or equal to 30° C., and at least one second film-forming polymer that is capable of forming a hydrophobic film at room temperature.

Another aspect of the invention is a mascara comprising, in a physiologically acceptable medium, at least one first semi-crystalline polymer with a melting point of greater than or equal to 30° C., and at least one second film-forming polymer capable of forming a hydrophobic film at room temperature.

Another aspect of the invention is a process for making a film comprising including in a cosmetic makeup or care composition for a keratin material at least one first semi-crystalline polymer with a melting point of greater than or equal to 30° C. and at least one second film-forming polymer capable of forming a hydrophobic film at room temperature; wherein said film is applied to said keratin material and is more resistant to removal by cold water than to removal by warm water having a temperature of at least 35° C.

Another aspect of the invention is a composition comprising, in a physiologically acceptable medium, at least one first semi-crystalline polymer having a melting point of greater than or equal to 30° C., and at least one second film-forming polymer that is capable of forming a hydrophobic film at room temperature; wherein said at least one semi-crystalline polymer does not comprise a polysaccharide backbone.

Yet another aspect of the invention is a composition comprising, in a physiologically acceptable medium, at least one first semi-crystalline polymer having a melting point of greater than or equal to 30° C., and at least one second film-forming polymer that is capable of forming a hydrophobic film at room temperature; wherein said semi-crystalline polymer is not polycaprolactone.

In accordance with the present invention, the expression "physiologically acceptable" should be understood as meaning a medium that is compatible with a keratin material, such as a cosmetic medium. According to one aspect, the composition according to the invention contains little emulsifier (surfactant), or is even free of emulsifier; for example, the emulsifier is present in an amount of less than 0.5% by weight relative to the total weight of the composition. The composition has good resistance to cold water.

In accordance with the present invention, the term "emulsifier" means any amphiphilic compound chosen from non-ionic amphiphilic compounds with an HLB (hydrophilic-lipophilic balance) of greater than or equal to 10, and ionic amphiphilic compounds whose hydrophilic portion comprises a counterion with a molar mass of greater than or equal to 50 g/mol.

The makeup removal with warm water is obtained using at least one semi-crystalline polymer with a thermal transition corresponding to its melting point.

Above its melting point, the semi-crystalline polymer, after its change of state, makes the film more water-sensitive: the film of makeup is made brittle on contact with warm water and by rubbing it, for example with the fingers or with a cloth or cotton wool, the film disintegrates readily or detaches from its support.

The at least one semi-crystalline polymer may be present in the composition in an amount ranging from 0.1% to 30% by weight, for example from 0.5% to 25% by weight. According to another embodiment, the semi-crystalline polymer is present in an amount ranging from 1% to 20% by weight, such as from 3% to 15% by weight, relative to the total weight of the composition.

In accordance with the present invention, the term "polymers" means compounds comprising at least two repeating units, such as, at least three repeating units. According to another aspect, the compounds comprise at least ten repeating units.

In accordance with the present invention, the expression "semi-crystalline polymer" means polymers comprising a crystallizable portion, crystallizable pendent chain, or crystallizable block in the skeleton, and an amorphous portion in the skeleton and having a temperature of first-order reversible phase change, for example of melting (solid-liquid transition). When the crystallizable portion is in the form of a crystallizable block of the polymer skeleton, the amorphous portion of the polymer is in the form of an amorphous block; in this case, the semi-crystalline polymer is a block copolymer, for example of the diblock, triblock or multiblock type comprising at least one crystallizable block and at least one amorphous block. The term "block" generally means at least five identical repeating units. The crystallizable block(s) is (are) then of different chemical nature from the amorphous block(s).

The semi-crystalline polymer according to the invention has a melting point of greater than or equal to 30° C., for example a melting point ranging from a 30° C. to 80° C. According to another aspect, the melting point ranges from 30° C. to 60° C. This melting point is a temperature of first-order change of state.

This melting point may be measured by any known method, for example by using a differential scanning calorimeter (DSC).

According to one aspect, the semi-crystalline polymer(s) referred to in the invention have a number-average molecular mass greater than or equal to 1,000.

According to another aspect, the semi-crystalline polymer(s) in the composition of the invention have a number-average molecular mass $\overline{M}n$ ranging from 2,000 to 800,000, for example from 3,000 to 500,000, and also from 4,000 to 150,000. According to another aspect, the number-average molecular mass ranges from less than 100,000, for example, from 4,000 to 99,000. According to one embodiment, they have a number-average molecular mass of greater than 5,600, for example, ranging from 5,700 to 99,000.

For the purposes of the invention, the expression "crystallizable chain or block" means a chain or block which, if it was obtained alone, would change from the amorphous state to the crystalline state reversibly, depending on whether one is above or below the melting point. For the purposes of the invention, a "chain" is a group of atoms, which are pendent or lateral relative to the polymer skeleton. A "block" is a group of atoms belonging to the skeleton, this group constituting one of the repeating units of the polymer. The expression "crystallizable chain" means a chain containing at least six carbon atoms.

According to one embodiment, the crystallizable block(s) or chain(s) of the semi-crystalline polymers represent at least 30% of the total weight of each polymer and better still at least 40%. The semi-crystalline polymers of the invention containing crystallizable blocks are block or multiblock polymers. They may be obtained by polymerizing a monomer containing reactive (or ethylenic) double bonds or by polycondensation. When the polymers of the invention are polymers containing crystallizable side chains, these side chains are advantageously in random form.

According to one embodiment, the semi-crystalline polymers of the invention are of synthetic origin. In addition, they may not comprise a polysaccharide skeleton. Generally, the crystallizable units (chains or blocks) of the semi-crystalline polymers according to the invention are derived from monomer(s) containing crystallizable block(s) or chain(s), used for the manufacture of the semi-crystalline polymers.

According to the invention, a semi-crystalline polymer with a low melting point is a semi-crystalline polymer with a melting temperature of less than 50° C. and a semi-crystalline polymer with a high melting point is a semi-crystalline polymer with a melting temperature at least equal to 50° C.

According to the invention, the low-melting semi-crystalline polymer and the high-melting semi-crystalline polymer are chosen from block copolymers comprising at least one crystallizable block and at least one amorphous block, homopolymers and copolymers bearing at least one crystallizable side chain per repeating unit, and mixtures thereof.

The semi-crystalline polymers that may be used in the invention may be chosen from, by way of non-limiting example:
- block copolymers of polyolefins of controlled crystallization, especially those whose monomers are described in EP-A-0 951 897 (the disclosure of which is incorporated herein by reference);
- polycondensates, for example, those of aliphatic or aromatic polyester type or of aliphatic/aromatic copolyester type;
- homopolymers and copolymers bearing at least one crystallizable side chain and homopolymers and copolymers bearing in the skeleton at least one crystallizable block, for instance those described in U.S. Pat. No. 5,156,911 (the disclosure of which is incorporated herein by reference);
- homopolymers and copolymers bearing at least one crystallizable side chain, for example those bearing fluoro group(s), as described in document WO-A-01/19333 (the disclosure of which is incorporated herein by reference), and mixtures thereof. In the last two cases, the crystallizable side chain(s) or block(s) are hydrophobic.

A) Semi-crystalline Polymers Containing Crystallizable Side Chains

Suitable non-limiting examples include those defined in U.S. Pat. No. 5,156,911 and WO-A-01/19333 (the disclosures of which are incorporated by reference herein). They are homopolymers and copolymers comprising from 50% to 100% by weight of units resulting from the polymerization of one or more monomers bearing a crystallizable hydrophobic side chain.

These homopolymers and copolymers are of any nature, provided that they meet the conditions mentioned previously.

They can result:
- from the polymerization, especially the free-radical polymerization, of one or more monomers containing reactive or ethylenic double bond(s) with respect to a polymerization, namely a vinyl, (meth)acrylic or allylic group,
- from the polycondensation of one or more monomers bearing co-reactive groups (carboxylic acid, sulphonic acid, alcohol, amine and isocyanate), such as, for example, polyesters, polyurethanes, polyethers, polyureas and polyamides.

In general, these polymers are chosen especially from homopolymers and copolymers resulting from the polymerization of at least one monomer containing crystallizable chain(s) that may be represented by formula X:

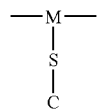

with M representing an atom of the polymer skeleton, S representing a spacer, and C representing a crystallizable group.

The crystallizable chains "—S—C" may be aliphatic or aromatic, and optionally fluorinated or perfluorinated. "S" represents a group chosen from $(CH_2)_n$, $(CH_2CH_2O)_n$, and $(CH_2O)_n$, which may chosen from linear, branched, and cyclic groups, with n being an integer ranging from 0 to 22. According to one embodiment, "S" is a linear group. According to one aspect, "S" and "C" are different.

When the crystallizable chains "—S—C" are hydrocarbon-based aliphatic chains, they comprise hydrocarbon-based alkyl chains containing at least 11 carbon atoms and not more than 40 carbon atoms, for example, not more than 24 carbon atoms. They can be chosen from alkyl chains containing at least 12 carbon atoms, for example $C_{14}$-$C_{24}$ alkyl chains. When they are fluoroalkyl or perfluoroalkyl chains, they contain at least six fluorinated carbon atoms and, according to one aspect, at least 11 carbon atoms, at least six of which carbon atoms are fluorinated.

As non-limiting examples of semi-crystalline polymers or copolymers containing crystallizable chain(s), mention may be made of those resulting from the polymerization of one or more of the following monomers: (meth)acrylates of saturated alkyls, with the alkyl group being $C_{14}$-$C_{24}$,; perfluoroalkyl (meth)acrylates with a $C_{11}$-$C_{15}$ perfluoroalkyl group; N-alkyl(meth)acrylamides with the alkyl group being $C_{14}$ to $C_{24}$, with or without a fluorine atom; vinyl esters containing alkyl or perfluoro(alkyl) chains with the alkyl group being $C_{14}$ to $C_{24}$ (with at least 6 fluorine atoms per perfluoroalkyl chain); vinyl ethers containing alkyl or perfluoro(alkyl) chains, with the alkyl group being $C_{14}$ to $C_{24}$ and at least 6 fluorine atoms per perfluoroalkyl chain; $C_{14}$ to $C_{24}$ alpha-olefins such as, for example, octadecene,; para-alkylstyrenes with an alkyl group containing from 12 to 24 carbon atoms; and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the invention are copolymers, they additionally contain from 0 to 50% of groups Y or Z resulting from the copolymerization:

α) of Y which is a polar or non-polar monomer or a mixture of the two:
  When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.
  When Y is a non-polar monomer, it may be an ester of the linear, branched or cyclic alkyl (meth)acrylate type, a vinyl ester, an alkyl vinyl ether, an alpha-olefin, styrene or styrene substituted with a $C_1$ to $C_{10}$ alkyl group, for instance α-methylstyrene, or a macromonomer of the polyorganosiloxane type containing vinyl unsaturation.

In accordance with the present invention, the term "alkyl" means a saturated group, such as of $C_8$ to $C_{24}$, except where otherwise mentioned, and such as of $C_{14}$ to $C_{24}$.

β) of Z which is a polar monomer or a mixture of polar monomers. In this case, Z has the same definition as the "polar Y" defined above.

According to one aspect, the semi-crystalline polymers containing a crystallizable side chain are alkyl (meth)acrylate or alkyl(meth)acrylamide homopolymers with an alkyl group as defined above, such as of $C_{14}$-$C_{24}$, copolymers of these monomers with a hydrophilic monomer, for example those of different nature from (meth)acrylic acid, for instance N-vinylpyrrolidone or hydroxyethyl (meth)acrylate, and mixtures thereof.

B) Polymers Bearing in the Skeleton at Least one Crystallizable Block

These polymers are especially block copolymers comprising at least two blocks of different chemical nature, one of which is crystallizable.

The block polymers defined in U.S. Pat. No. 5,156,911 (the disclosure of which is incorporated herein by reference) may be used;

Block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, copoly(ethylene/norbornene) blocks and (ethylene/propylene/ethylidene-norbornene) block terpolymers. Those resulting from the block copolymerization of at least two $C_2$-$C_{16}$, for example $C_2$-$C_{12}$, further $C_4$-$C_{12}$ α-olefins, such as those mentioned above, and block bipolymers of ethylene and of 1-octene, may also be used.

The copolymers may be copolymers containing at least one crystallizable block, the copolymer residue being amorphous (at room temperature). These copolymers may also contain two crystallizable blocks of different chemical nature. Suitable copolymers include those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) polyester, for instance poly(alkylene terephthalate), b) polyolefin, for instance polyethylenes or polypropylenes.

Amorphous and lipophilic block, for instance amorphous polyolefins or copoly(olefin)s such as poly(isobutylene), hydrogenated polybutadiene or hydrogenated poly(isoprene).

As examples of such copolymers containing a crystallizable block and a separate amorphous block, mention may be made of:

α) poly(ε-caprolactone)-b-poly(butadiene) block copolymers, for example used hydrogenated, such as those described in the article "Melting Behavior of Poly(ε-caprolactone)-block-polybutadiene copolymers" from S. Nojima, *Macromolecules,* 32, 3727-3734 (1999) (the disclosure of which is incorporated herein by reference)

β) the hydrogenated block or multiblock poly(butylene terephthalate)-b-poly(isoprene) block copolymers cited in the article "Study of Morphological and Mechanical Properties of PP/PBT" by Boutevin et al., *Polymer Bulletin,* 34, 117-123 (1995) (the disclosure of which is incorporated by reference herein), γ) the poly(ethylene)-b-copoly(ethylene/propylene) block copolymers cited in the articles "Morphology of Semi-Crystalline Block Copolymers of ethylene-(ethylene-alt-propylene)" by P. Rangarajan et al., *Macromolecules,* 26, 4640-4645 (1993) and "Polymer Aggregates with Crystalline Cores: the System poly(ethylene)-poly(ethylene-propylene)" by P. Richter et al., *Macromolecules,* 30, 1053-1068 (1997), δ) the poly(ethylene)-b-poly(ethylethylene) block copolymers cited in the general article "Crystallization in Block Copolymers" by I. W. Hamley, *Advances in Polymer Science,* Vol. 148, 113-137 (1999) (the disclosures of which are all incorporated by reference herein).

The semi-crystalline polymers in the composition of the invention may or may not be partially crosslinked, provided that the degree of crosslinking does not interfere with their dissolution or dispersion in the liquid fatty phase by heating above their melting point. It may then be a chemical crosslinking, by reaction with a multifunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer skeleton; or to a phase separation between the crystallizable blocks and the amorphous blocks borne by the polymer.

According to one aspect, the semi-crystalline polymers in the composition according to the invention are non-crosslinked.

According to one embodiment of the invention, the polymer is chosen from copolymers resulting from the polymerization of at least one monomer containing a crystallizable chain chosen from saturated $C_{14}$ to $C_{24}$ alkyl (meth)acrylates; $C_{11}$ to $C_{15}$ perfluoroalkyl (meth)acrylates; $C_{14}$ to $C_{24}$ N-alkyl(meth)acrylamides substituted or unsubstituted with at least one fluorine atom, vinyl esters containing $C_{14}$ to $C_{24}$ alkyl or perfluoroalkyl chains, vinyl ethers comprising chains chosen from $C_{14}$ to $C_{24}$ alkyl and perfluoroalkyl chains, $C_{14}$ to $C_{24}$ alpha-olefins, para-alkylstyrenes with an alkyl group containing from 12 to 24 carbon atoms, with at least one optionally fluorinated $C_1$ to $C_{10}$ monocarboxylic acid ester or amide, which may be represented by the following formula:

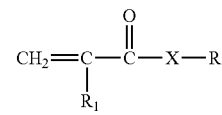

in which $R_1$ is chosen from H and $CH_3$, R is chosen from optionally fluorinated $C_1$-$C_{10}$ alkyl groups and X is chosen from O, NH, and $NR_2$ in which $R_2$ is chosen from optionally fluorinated $C_1$-$C_{10}$ alkyl groups.

According to one embodiment of the invention, the polymer is derived from a monomer containing a crystallizable chain, chosen from saturated $C_{14}$ to $C_{22}$ alkyl (meth)acrylates.

For example, the semi-crystalline polymer present in the composition according to the invention may not be a poly-caprolactone.

As suitable non-limiting examples of the structuring semi-crystalline polymers that may be used in the composition according to the invention, mention may be made of the products Intelimer® from the company Landec, described in the brochure "Intelimer® polymers", Landec IP22 (Rev. 4-97) (the disclosure of which is incorporated by reference herein). These polymers are in solid form at room temperature (25° C.). They bear crystallizable side chains and have the formula X above.

The semi-crystalline polymers may be:

those described in Examples 3, 4, 5, 7, 9 and 13 of U.S. Pat. No. 5,156,911 (the disclosure of which is incorporated by reference herein) containing a —COOH group, resulting from the copolymerization of acrylic acid and of $C_5$ to $C_{16}$ alkyl (meth)acrylate and, for example, the copolymerization:

- of acrylic acid, of hexadecyl acrylate and of isodecyl acrylate in a 1/16/3 weight ratio,
- of acrylic acid and of pentadecyl acrylate in a 1/19 weight ratio,
- of acrylic acid, of hexadecyl acrylate and of ethyl acrylate in a 2.5/76.5/20 weight ratio,
- of acrylic acid, of hexadecyl acrylate and of methyl acrylate in a 5/85/10 weight ratio,
- of acrylic acid and of octadecyl methacrylate in a 2.5/97.5 weight ratio,
- of hexadecyl acrylate, of polyethylene glycol methacrylate monomethyl ether containing 8 ethylene glycol units, and of acrylic acid in an 8.5/1/0.5 weight ratio.

It is also possible to use the structure "O" from National Starch, as described in U.S. Pat. No. 5,736,125, (the disclosure of which is incorporated herein by reference) with a melting point of 44° C., and also semi-crystalline polymers with crystallizable pendent chains comprising fluoro groups, as described in Examples 1, 4, 6, 7 and 8 of WO-A-01/19333.

It is also possible to use low-melting semi-crystalline polymers obtained by copolymerization of stearyl acrylate and of acrylic acid or of NVP, as described in document U.S. Pat. No. 5,519,063 or EP-A-550,745 (the disclosures of which are incorporated herein by reference), as well as those described in Examples 1 and 2 below, for the preparation of polymers, with a melting point of 40° C. and 38° C., respectively.

It is also possible to use semi-crystalline polymers obtained by copolymerization of behenyl acrylate and of acrylic acid or of NVP, as described in U.S. Pat. No. 5,519,063 and EP-A-550 745, and as well as those described in Examples 3 and 4 below, for the preparation of polymers, with a melting point of 60° C. and 58° C., respectively.

According to one embodiment, the low-melting semi-crystalline polymers and/or those with a high melting point do not comprise a carboxylic group.

According to embodiment, the composition also comprises a film-forming polymer capable of forming a hydrophobic film, also known as the second film-forming polymer.

The expression "film-forming polymer capable of forming a hydrophobic film" means a polymer whose film has a solubility in water at 25° C. of less than 1% by weight.

The second film-forming polymer may be chosen from synthetic polymers, for example free-radical polymers or polycondensates, and polymers of natural origin, and mixtures thereof.

The term "free-radical film-forming polymer" means a polymer obtained by polymerization of monomers containing unsaturation, especially ethylenic unsaturation (unlike polycondensates).

The film-forming polymers of free-radical type may include vinyl polymers or copolymers, for example acrylic polymers.

The vinyl film-forming polymers may result from the polymerization of monomers with ethylenic unsaturation containing at least one acidic group and/or esters of these acid monomers and/or amides of these acid monomers.

As monomers bearing an acidic group, it is possible to use α,β-ethylenic unsaturated carboxylic acids such as acrylic acid, methacrylic acid, crotonic acid, maleic acid or itaconic acid. According to one embodiment, (Meth)acrylic acid and crotonic acid are used, and according to another embodiment, (meth)acrylic acid.

The esters of acid monomers are advantageously chosen from (meth)acrylic acid esters (also referred to as (meth)acrylates), for example alkyl (meth)acrylates, including alkyl (meth)acrylates of a $C_1$-$C_{30}$ alkyl, which may be linear, branched or cyclic, for example $C_1$-$C_{20}$, aryl (meth)acrylates, for example of a $C_6$-$C_{10}$ aryl, and hydroxyalkyl (meth)acrylates, for example of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are suitable include the alkyl (meth)acrylates.

According to the present invention, the alkyl group of the esters may be either fluorinated or perfluorinated, that is to say that some or all of the hydrogen atoms of the alkyl group are replaced with fluorine atoms.

Non-limiting examples of amides of the acid monomers that may be mentioned include (meth)acrylamides for example N-alkyl(meth)acrylamides, including those of a $C_1$-$C_{20}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of at least one monomer chosen from vinyl esters, olefins (including fluoroolefins), vinyl ethers and styrene monomers. These monomers may be polymerized with acid monomers and/or esters thereof and/or amides thereof, such as those mentioned above.

Non-limiting examples of vinyl esters that may be mentioned are vinyl acetate, vinyl neodecanoate, vinyl pivalate, vinyl benzoate and vinyl t-butylbenzoate.

Suitable non-limiting examples of olefins that may be mentioned include ethylene, propylene, butene, isobutene, octene, octadecene, and poly(fluorinated olefins), such as tetrafluoroethylene, vinylidene fluoride, hexafluoropropene or chlorotrifluoroethylene.

Styrene monomers that may be mentioned are styrene and α-methylstyrene.

The list of monomers given is not limiting and it is possible to use any monomer known to those skilled in the art that falls within the categories of acrylic and vinyl monomers (including monomers modified with a silicone chain).

Among the polycondensates that may be used as a film-forming polymer, mention may thus be made of anionic, cationic, nonionic or amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The film-forming polyurethane may be, for example, an aliphatic, cycloaliphatic or aromatic polyurethane, polyurea/urethane or polyurea copolymer, comprising, alone or as a mixture:

- at least one sequence of aliphatic and/or cycloaliphatic and/or aromatic polyester origin, and/or
- at least one branched or unbranched silicone block, for example polydimethylsiloxane or polymethylphenylsiloxane, and/or
- at least one block comprising fluorinated groups.

Suitable examples of film-forming polycondensates that may also be mentioned include polyesters, polyesteramides, fatty-chain polyesters, polyamides and epoxyester resins, resins resulting from the condensation of formaldehyde with an arylsulphonamide, and arylsulphonamide-epoxy resins.

The polyesters may be obtained, in a known manner, by polycondensation of dicarboxylic acids with polyols, for example diols.

The dicarboxylic acid may be aliphatic, alicyclic or aromatic. Non-limiting examples of such acids which may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, the ones suitably chosen include phthalic acid, isophthalic acid and terephthalic acid.

The diol may be chosen from aliphatic, alicyclic and aromatic diols. The diol used may be chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner similar to that of the polyesters, by polycondensation of diacids with diamines or with amino alcohols. Diamines that may be used include ethylenediamine, hexamethylenediamine, meta-phenylenediamine and para-phenylenediamine. An amino alcohol that may be used is monoethanolamine.

The polyester may also comprise at least one monomer bearing at least one group —$SO_3M$, with M being chosen from a hydrogen atom, an ammonium ion $NH_4^+$ and a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may also be used.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. Examples of difunctional aromatic monomers also bearing a group —$SO_3M$ that may be mentioned include: sulphoisophthalic acid, sulphoterephthalic acid, sulphophthalic acid, 4-sulphonaphthalene-2,7-dicarboxylic acid.

In the compositions which are the subject of the invention, it is possible to use copolymers based on isophthalate/sulphoisophthalate, as well as copolymers obtained by condensation of di-ethylene glycol, cyclohexanedimethanol, isophthalic acid or sulphoisophthalic acid. Such polymers are sold, for example, under the brand name Eastman AQ by the company Eastman Chemical Products.

The synthetic hydrophobic polymer may also be a silicone polymer, for example polyorganopolysiloxane.

The polymers of natural origin, which are optionally modified, may be chosen from shellac resin, sandarac gum, dammar resins, elemi resins, copal resins, cellulose polymers such as nitrocellulose, cellulose acetate, cellulose acetobutyrate, cellulose acetopropionate or ethylcellulose, and mixtures thereof.

Film-forming polymers that may also be used are film-forming silicone polymers.

According to one embodiment of the invention, the second polymer may be present in the form of solid particles dispersed in an aqueous medium. The expression "polymer in the form of particles in aqueous dispersion", which is generally known as a latex or pseudolatex, means a phase containing water and optionally a water-soluble compound, in which is directly dispersed the polymer in the form of particles.

The size of the polymer particles in aqueous dispersion may range from 10 nm to 500 nm, for example from 20 nm to 300 nm.

The aqueous medium may consist essentially of water or may also comprise a mixture of water and of water-miscible solvent, for instance lower monoalcohols containing from 1 to 5 carbon atoms, glycols containing from 2 to 8 carbon atoms, $C_3$-$C_4$ ketones or $C_2$-$C_4$ aldehydes. In practice, it represents from 5% to 94.9% by weight relative to the total weight of the composition.

Suitable non-limiting examples of film-forming polymers in aqueous dispersion which may be used include the acrylic polymers sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, or polyurethanes such as the polyester-polyurethanes sold under the names "Avalure UR-405®", "Avalure UR-410®", "Avalure UR-425®" and "Sancure 2060®" by the company Goodrich, the polyether-polyurethanes sold under the names "Sancure 878®" and "Avalure UR-450®" by the company Goodrich and "Neorez R 970®" by the company ICI and the polyurethane-acrylics sold under the name Neorez R-989® by the company Avecia-Neoresins.

It is also possible to use "alkali-soluble" polymers, taking care to ensure that the pH of the composition is adjusted so as to keep these polymers in the form of particles in aqueous dispersion.

The composition according to the invention may comprise a film-forming auxiliary agent that promotes the formation of a film with the particles of the film-forming polymer. Such a film-forming agent may be chosen from any compounds known to those skilled in the art as being capable of fulfilling the desired function, and may be chosen in particular from plasticizers and coalescers.

According to a second embodiment variant of the invention, the second film-forming polymer, also known as the liposoluble polymer, may be present in dissolved form in a liquid fatty phase.

Non-limiting examples of liposoluble polymers that may be mentioned include polymers corresponding to formula (I) below:

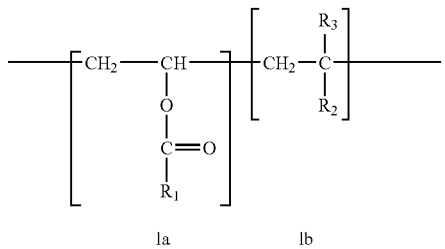

in which:
- $R_1$ represents a linear or branched saturated hydrocarbon-based chain containing from 1 to 19 carbon atoms;
- $R_2$ represents a radical taken from the group consisting of:
a) —O—CO—$R_4$, $R_4$ having the same meaning as $R_1$ but is different from $R_1$ in the same copolymer,
b) —$CH_2$—$R_5$, $R_5$ representing a linear or branched saturated hydrocarbon-based chain containing from 5 to 25 carbon atoms,
c) —O—$R_6$, $R_6$ representing a saturated hydrocarbon-based chain containing from 2 to 18 carbon atoms, and
d) —$CH_2$—O—CO—$R_7$, $R_7$ representing a linear or branched saturated hydrocarbon-based chain containing from 1 to 19 carbon atoms,
- $R_3$ represents a hydrogen atom when $R_2$ represents the radicals a), b) or c) or $R_3$ represents a methyl radical when $R_2$ represents a radical d), the said copolymer needing to consist of at least 15% by weight of at least one monomer derived from a unit (Ia) or from a unit (Ib) in which the saturated or branched hydrocarbon-based chains contain at least 7 carbon atoms.

The copolymers of formula (I) result from the copolymerization of at least one vinyl ester (corresponding to the unit Ia) and of at least one other monomer (corresponding to the unit Ib), which may be an α-olefin, an alkyl vinyl ether or an allylic or methallylic ester.

When, in the unit (Ib), $R_2$ is chosen from the radicals —$CH_2$—$R_5$, —O—$R_6$ or —$CH_2$—O—CO—$R_7$ as defined above, the copolymer of formula (I) may consist of from 50 mol % to 95 mol % of at least one unit (Ia) and of from 5 mol % to 50 mol % of at least one unit (Ib).

The copolymers of formula (I) may also result from the copolymerization of at least one vinyl ester and of at least one other vinyl ester that is different from the first ester. In this case, these copolymers may consist of from 10 mol % to 90 mol % of at least one unit (Ia) and of from 10 mol % to 90 mol % of at least one unit (Ib) in which $R_2$ represents a radical —O—CO—$R_4$.

Among the vinyl esters leading to the unit of formula (Ia), or to the unit of formula (Ib) in which $R_2$=—O—CO—$R_4$, mention may be made of vinyl acetate, vinyl propionate, vinyl butanoate, vinyl octanoate, vinyl decanoate, vinyl laurate, vinyl stearate, vinyl isostearate, vinyl 2,2-dimethyloctanoate and vinyl dimethylpropionate.

Among the α-olefins leading to the unit of formula (Ib) in which $R_2$=—$CH_2$—$R_5$, mention may be made of 1-octene, 1-dodecene, 1-octadecene and 1-eicosene, and mixtures of α-olefins containing from 22 to 28 carbon atoms.

Among the alkyl vinyl ethers leading to the unit of formula (Ib) in which $R_2$=—O—$R_6$, mention may be made of ethyl vinyl ether, n-butyl vinyl ether, isobutyl vinyl ether, decyl vinyl ether, dodecyl vinyl ether, cetyl vinyl ether and octadecyl vinyl ether.

Among the allylic or methallylic esters leading to the unit of formula (Ib) in which $R_2$=—$CH_2$—O—CO—$R_7$, mention may be made of allyl and methallyl acetates, propionates, dimethylpropionates, butyrates, hexanoates, octanoates, decanoates, laurates, 2,2-dimethylpentanoates, stearates and eicosanoates.

The copolymers of formula (I) may also be crosslinked using certain types of crosslinking agents that are intended to substantially increase their molecular weight.

This crosslinking is carried out during the copolymerization and the crosslinking agents may be either of the vinyl type or of the allylic or methallylic type. Among these crosslinking agents that may be mentioned are tetraallyloxyethane, divinylbenzene, divinyl octanedioate, divinyl dodecanedioate and divinyl octadecanedioate.

Among the various copolymers of formula (I) which may be used in the composition according to the invention, mention may be made of the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Liposoluble film-forming polymers which may also be mentioned include liposoluble homopolymers, for example those resulting from the homopolymerization of vinyl esters containing from 9 to 22 carbon atoms or of alkyl acrylates or methacrylates, the alkyl radicals containing from 10 to 20 carbon atoms.

Such liposoluble homopolymers may be chosen from polyvinyl stearate, polyvinyl stearate crosslinked with divinylbenzene, with diallyl ether or with diallyl phthalate, polystearyl (meth)acrylate or polylauryl (meth)acrylate, these poly(meth)acrylates possibly being crosslinked with the aid of ethylene glycol dimethacrylate or tetraethylene glycol dimethacrylate.

The liposoluble copolymers and homopolymers defined above are known and are disclosed in, for example, patent application FR-A-2 262 303 (the disclosure of which is incorporated by reference herein); they may have a weight-average molecular weight ranging from 2,000 to 500,000 and preferably from 4,000 to 200,000.

As liposoluble film-forming polymers which may be used in the invention, mention may also be made of polyalkylenes and $C_2$-$C_{20}$ alkene copolymers, other than the polyolefin wax defined in a), for instance polybutene, alkylcelluloses with a linear or branched, saturated or unsaturated $C_1$ to $C_8$ alkyl radical, for instance ethylcellulose and propylcellulose, vinylpyrrolidone (VP) copolymers and copolymers of vinylpyrrolidone and of $C_2$ to $C_{40}$, for example $C_3$ to $C_{20}$ alkene. As non-limiting examples of VP copolymers that may be used in the invention, mention may be made of VP/vinyl acetate, VP/ethyl methacrylate, butylated polyvinylpyrrolidone (PVP), VP/ethyl methacrylate/methacrylic acid, VP/hexadecene, VP/triacontene, VP/styrene or VP/acrylic acid/lauryl methacrylate copolymer.

The liquid fatty phase may comprise a volatile liquid fatty phase, optionally as a mixture with a non-volatile liquid fatty phase.

The expression "volatile fatty phase" means any non-aqueous medium that is capable of evaporating from the skin in less than one hour. This volatile phase may comprise oils with a vapour pressure, at room temperature and atmospheric pressure, ranging from $10^{-3}$ to 300 mmHg (0.13 Pa to 40 000 Pa).

The liquid fatty phase in which the polymer is dispersed may be comprised of any physiologically acceptable and cosmetically acceptable oil chosen from, for example, oils of mineral, animal, plant or synthetic origin, carbon-based oils, hydrocarbon-based oils, fluoro oils and/or silicone oils, alone or as a mixture provided that they form a homogeneous and stable mixture and provided that they are compatible with the intended use.

The total liquid fatty phase of the composition may range from 5% to 98% by weight relative to the total weight of the composition, for example from 20% to 85% by weight. The non-volatile part may range from 0 to 80% (for example from 0.1% to 80%) of the total weight of the composition, and also from 1% to 50%.

As liquid fatty phase which may be used in the invention, mention may thus be made of fatty acid esters, higher fatty acids, higher fatty alcohols, polydimethylsiloxanes (PDMSs), which are optionally phenylated such as phenyltrimethicones, or which are optionally substituted with aliphatic and/or aromatic groups, which may be fluorinated, or are optionally substituted with functional groups such as hydroxyl, thiol and/or amine groups; polysiloxanes modified with fatty acids, with fatty alcohols or with polyoxyalkylenes, fluorosilicones and perfluoro oils.

For example, one or more oils that are volatile at room temperature may be used. After evaporating off these oils, a non-sticky, supple film-forming deposit is obtained. These volatile oils also make it easier to apply the composition to keratin fibres such as the eyelashes.

These volatile oils can be hydrocarbon-based oils or silicone oils optionally comprising alkyl or alkoxy groups at the end of the silicone chain or pendent on the chain.

As volatile silicone oils which can be used in the invention, mention may be made of linear or cyclic silicones containing from 2 to 7 silicon atoms, these silicones optionally comprising alkyl or alkoxy groups containing from 1 to 10 carbon atoms. Mention may be made of octamethylcyclotetrasiloxane, decamethylcyclopentasiloxane, hexadecamethylcyclohexasiloxane, heptamethylhexyltrisiloxane and heptamethyloctyltrisiloxane.

Volatile hydrocarbon-based oils that may be mentioned include $C_8$-$C_{16}$ isoparaffins such as Isopars and Permetyls, as well as isododecane.

These volatile oils can be present in the composition in an amount ranging from 5% to 94.9% relative to the total weight of the composition, for example from 20% to 85%.

The second film-forming polymer may be present in a solids content ranging from 5% to 60% by weight relative to the total weight of the composition, for example from 10% to 45% by weight, and also from 15% to 35% by weight.

For example, the first semi-crystalline polymer and the second film-forming polymer may be present in the composition in a second film-forming polymer/first semi-crystalline polymer weight ratio ranging from 90/10 to 10/90, such as from 70/30 to 30/70 and further such as from 60/40 to 40/60.

The composition may also comprise at least one dyestuff, for instance pulverulent compounds and/or liposoluble dyes, for example in a proportion of from 0.01% to 50% relative to the total weight of the composition. The pulverulent compounds may be chosen from the pigments and/or nacres usually used in cosmetic compositions. For example, the pulverulent compounds represent from 0.1% to 25% of the total weight of the composition, such as from 1% to 20%.

The pigments may be white or colored, and mineral and/or organic. Among the mineral pigments which may be mentioned are titanium dioxide, optionally surface-treated, zirconium oxide and cerium oxide, and also iron oxide, chromium oxide, manganese violet, ultramarine blue, chromium hydrate and ferric blue. Among the organic pigments that may be mentioned are carbon black, pigments of D & C type and lakes based on cochineal carmine or on barium, strontium, calcium or aluminium.

The nacreous pigments may be chosen from white nacreous pigments such as mica coated with titanium or with bismuth oxychloride, colored nacreous pigments such as titanium mica with iron oxides, titanium mica with, ferric blue or with chromium oxide, titanium mica with an organic pigment of the abovementioned type, and also nacreous pigments based on bismuth oxychloride.

The composition may also comprise fillers, which may be chosen from those that are well known to those skilled in the art and which are commonly used in cosmetic compositions. The fillers may be mineral or organic, and lamellar or spherical. Mention may be made of talc, mica, silica, kaolin, Nylon powder (Orgasol from Atochem), poly-β-alanine powder, polyethylene powder, Teflon, lauroyllysine, starch, boron nitride, tetrafluoroethylene polymer powders, hollow microspheres such as Expancel (Nobel Industrie), Polytrap (Dow Corning), silicone resin microbeads (for example Tospearls from Toshiba), precipitated calcium carbonate, magnesium carbonate, magnesium hydrocarbonate, hydroxyapatite, hollow silica microspheres (Silica Beads from Maprecos), glass or ceramic microcapsules, metal soaps derived from organic carboxylic acids containing from 8 to 22, for example from 12 to 18 carbon atoms, for example zinc stearate, magnesium stearate, lithium stearate, zinc laurate or magnesium myristate.

The composition may also contain any additive usually used in such compositions, such as thickeners, preserving agents, fragrances, sunscreens, free-radical scavengers, waxes, oils, moisturizers, vitamins, proteins, plasticizers, sequestrants, ceramides, acidifying or basifying agents, or emollients.

Needless to say, a person skilled in the art will take care to select this or these optional additional compound(s), and/or the amount thereof, such that the advantageous properties of the composition according to the invention are not, or are not substantially, adversely affected by the addition envisaged.

The invention is illustrated in greater detail in the examples that follow.

Test to Measure the Water Resistance of a Film

A layer of composition 300 μm thick (before drying) with an area of 9 cm×9 cm is spread onto a glass plate with an area of 10 cm×10 cm, is left to dry for 24 hours at 30° C. and 50% relative humidity. After drying, the plate is placed in a crystallizing vessel with a diameter of 19 cm and a volume of 2 litres filled with 1 litre of water, placed on a magnetic hotplate-stirrer sold under the name RCT basic by the company IKA Labortechnik.

A smooth PTFE cylindrical magnetic bar (length 6 cm; diameter 1 cm) is then placed on the film. The stirring speed is set to position 5. The water temperature is controlled using a thermometer at a temperature of 20° C. or 40° C. At time $t_0=0$, stirring is started. The time t (expressed in minutes) after which the film begins to detach or loosen from the plate or when a hole the size of the magnetic stirring bar is observed, i.e. when the hole has a diameter of 6 cm, is measured. The test is stopped if the film remains intact at the end of 2 hours. The water resistance of the film corresponds to the time t measured, expressed in minutes.

Test of Water Uptake of a Film

A layer of composition 300 µm thick (before drying) placed on a plate is spread out and then dried for 24 hours at 30° C. and at 50% relative humidity; pieces about 1 cm² cut out of the dry film are weighed (mass measurement M1) and then immersed in water, at 20° C. or at 40° C., for 10 minutes; after immersion, the piece of film is wiped to remove the excess water from the surface and then weighed (mass measurement M2). The difference M2−M1 corresponds to the amount of water absorbed by the film.

The water uptake of the film is equal to $[(M2-M1)/M1] \times 100$ and is expressed as a weight percentage of water relative to the weight of the film.

EXAMPLES OF MANUFACTURE OF SEMI-CRYSTALLINE POLYMERS

Example 1

Acidic Polymer with a Melting Point of 40° C.

120 g of Parleam are placed in a 1 l reactor equipped with a central paddle stirrer, a condenser and a thermometer, and are heated from room temperature to 80° C. over 45 minutes. At 80° C., the following mixture $C_1$ is introduced over 2 hours:

40 g of cyclohexane+4 g of Triganox 141 [2,5-bis(2-ethyl-hexanoylperoxy)-2,5-dimethylhexane].

30 minutes after the start of the addition of the mixture $C_1$, the mixture $C_2$ is introduced over 1 hour 30 minutes, consisting of:

190 g of stearyl acrylate+10 g of acrylic acid+400 g of cyclohexane.

At the end of the two additions, the mixture is stirred for a further 3 hours at 80° C. and all the cyclohexane present in the reaction medium is then distilled off at atmospheric pressure.

The polymer is thus obtained at 60% by weight of active material in Parleam. Its weight-average molecular mass $M_w$ is 35 000, expressed as polystyrene equivalent, and its melting point $T_m$ is 40° C.±1° C., measured by DSC.

Example 2

Basic Polymer with a Melting Point of 38° C.

The same procedure as in Example 1 is applied, except that N-vinylpyrrolidone is used instead of acrylic acid.

The polymer obtained is at 60% by weight of active material in Parleam, its weight-average molecular mass $M_w$ is 38 000 and its $T_m$ is 38° C.

Examples 3 and 4

The semi-crystalline polymers of Examples 1 and 2 were tested in the following composition:

| | |
|---|---|
| Polyurethane as an aqueous dispersion, sold under the name Avalure UR 425 by the company Goodrich, at an active material content of 49% by weight | 14 g A.M. |
| Semi-crystalline polymer | 10 g A.M. |
| Hydroxyethylcellulose | 1.9 g |
| Black iron oxide | 5 g |
| Propylene glycol | 5 g |
| Preserving agents | qs |
| Water | qs 100 g |

For each composition, the resistance to cold water (20° C.) (noted as RES) and to warm water (40° C.), and the water uptake (noted as UPT) of the film at 20° C. and at 40° C., were measured in accordance with the protocols described above.

The following results were obtained:

| Example | 3 | 4 |
|---|---|---|
| Semi-crystalline polymer | Example 1 | Example 2 |
| RES 20° C. (in minutes) | 40 | 100 |
| RES 40° C. (in minutes) | 3 | 15 |
| UPT 20° C. (in %) | 30.8 | 20.4 |
| UPT 40° C. (in %) | 54.5 | 32.5 |

It is found that, for each composition, the film of makeup is much less resistant in the presence of water at 40° C. (warm water) than in the presence of water at room temperature (cold water). Furthermore, the film takes up more water at a temperature of 40° C. than at 20° C. The makeup is thus resistant to cold water and is easy to remove with warm water.

Each composition was also applied to the eyelashes: the makeup result obtained is easy to remove with warm water (40° C.) in the form of a sleeve.

Example 5

A mascara having the composition below was prepared:

| | |
|---|---|
| Polyurethane as an aqueous dispersion, sold under the name Avalure UR 425 by the company Goodrich, at an active material content of 49% by weight | 18 g A.M. |
| Semi-crystalline polymer of Example 2 | 15 g A.M. |
| Hydroxyethylcellulose | 1.9 g |
| Black iron oxide | 5 g |
| Propylene glycol | 5 g |
| Preserving agents | qs |
| Water | qs 100 g |

This composition forms a film having a resistance (noted as RES) to cold water (20° C.) equal to 80 minutes, and a resistance to warm water (40° C.) equal to 12 minutes, measured in accordance with the protocol described above.

It is found that the film of makeup obtained is much less resistant in the presence of water at 40° C. (warm water) than in the presence of water at room temperature (cold water). The makeup is thus resistant to cold water and is easier to remove with warm water.

Each composition was also applied to the eyelashes: the makeup result obtained is easy to remove with warm water (40° C.) in the form of a sheath.

What is claimed is:

1. A composition comprising, in a physiologically acceptable medium, at least one first semi-crystalline polymer having a melting point of greater than or equal to 30° C., and at least one second film-forming polymer that is capable of forming a hydrophobic film at room temperature, wherein the at least one first semi-crystalline polymer and the at least one second film-forming polymer are present in said composition in an at least one second film-forming polymer/at least one first semi-crystalline polymer weight ratio ranging from 90:10 to 10:90.

2. The composition of claim 1, wherein the at least one first semi-crystalline polymer has a melting point ranging from 30° C. to 80° C.

3. The composition of claim 2, wherein the at least one first semi-crystalline polymer has a melting point ranging from 30° C. to 60° C.

4. The composition of claim 1, wherein the at least one first semi-crystalline polymer has a number-average molecular mass of greater than or equal to 1,000.

5. The composition of claim 1, wherein the at least one first semi-crystalline polymer has a number-average molecular mass ranging from 3,000 to 500,000.

6. The composition of claim 5, wherein the at least one first semi-crystalline polymer has a number-average molecular mass ranging from 4,000 to 150,000.

7. The composition of claim 1, wherein the at least one first semi-crystalline polymer comprises i) a polymer skeleton; and ii) at least one crystallizable side chain and/or at least one crystallizable organic block that forms part of the skeleton of said at least one first semi-crystalline polymer.

8. The composition of claim 1, wherein the at least one first semi-crystalline polymer is chosen from block copolymers comprising at least one crystallizable block and at least one amorphous block, and homopolymers and copolymers bearing at least one crystallizable side chain per repeating unit.

9. The composition of claim 8, wherein in said block copolymers, there are at least two crystallizable blocks that are not identical and/or there are at least two amorphous blocks that are not identical.

10. The composition of claim 1, wherein the at least one first semi-crystalline polymer is chosen from:
block copolymers of polyolefins of controlled crystallization;
aliphatic and aromatic polyester polycondensates and aliphatic/aromatic copolyesters; and
homopolymers and copolymers bearing at least one crystallizable side chain.

11. The composition of claim 1, wherein the at least one first semi-crystalline polymer is chosen from homopolymers and copolymers comprising from 50% to 100% by weight of units resulting from the polymerization of at least one monomer bearing at least one crystallizable hydrophobic side chain.

12. The composition of claim 1, wherein the at least one first semi-crystalline polymer is chosen from block homopolymers and copolymers resulting from the polymerization of at least one monomer comprising at least one amorphous block, and at least one crystallizable side chain per repeating unit, of formula X:

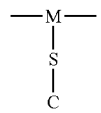

wherein M represents an atom of a polymer skeleton, S represents a spacer, C represents a crystallizable group, and "—S—C" is chosen from optionally fluorinated and perfluorinated alkyl chains comprising at least 11 carbon atoms.

13. The composition of claim 1, wherein the at least one first semi-crystalline polymer is chosen from polymers resulting from the polymerization of at least one monomer chosen from acrylic acid, methacrylic acid, crotonic acid, itaconic acid, maleic acid, and maleic anhydride.

14. The composition of claim 1, wherein the at least one first semi-crystalline polymer is chosen from homopolymers and copolymers resulting from the polymerization of at least one monomer comprising a crystallizable block, chosen from saturated $C_{14}$-$C_{24}$ alkyl (meth)acrylates; $C_{11}$-$C_{15}$ perfluoroalkyl (meth)acrylates; $C_{14}$ to $C_{24}$ N-alkyl(meth)acrylamides unsubstituted or substituted with at least one fluorine atom; vinyl esters comprising chains chosen from $C_{14}$ to $C_{24}$ alkyl and perfluoroalkyl chains; vinyl ethers comprising chains chosen from $C_{14}$ to $C_{24}$ alkyl and perfluoroalkyl chains; $C_{14}$ to $C_{24}$ alpha-olefins; and para-alkylstyrenes with an alkyl group comprising from 12 to 24 carbon atoms.

15. The composition of claim 1, wherein the at least one first semi-crystalline polymer is chosen from copolymers resulting from the polymerization of at least one monomer containing a crystallizable chain, chosen from saturated $C_{14}$ to $C_{24}$ alkyl (meth)acrylates; $C_{11}$ to $C_{15}$ perfluoroalkyl (meth)acrylates; $C_{14}$ to $C_{24}$ N-alkyl(meth)acrylamides unsubstituted or substituted with at least one fluorine atom; vinyl esters comprising chains chosen from $C_{14}$ to $C_{24}$ alkyl and perfluoroalkyl chains; vinyl ethers comprising chains chosen from $C_{14}$ to $C_{24}$ alkyl and perfluoroalkyl chains; $C_{14}$ to $C_{24}$ alpha-olefins; and para-alkylstyrenes with an alkyl group comprising from 12 to 24 carbon atoms with at least one monomer chosen from optionally fluorinated $C_1$ to $C_{10}$ monocarboxylic acid ester and amides.

16. The composition of claim 1, wherein the at least one first semi-crystalline polymer is chosen from $C_{14}$ to $C_{24}$ alkyl (meth)acrylate and $C_{14}$ to $C_{24}$ alkyl(meth)acrylamide homopolymers, and copolymers of at least one monomer chosen from $C_{14}$ to $C_{24}$ alkyl (meth)acrylate and $C_{14}$ to $C_{24}$ alkyl(meth)acrylamide homopolymers with at least one hydrophilic monomer.

17. The composition of claim 1, wherein the at least one first semi-crystalline polymer is chosen from copolymers of at least one monomer chosen from $C_{14}$ to $C_{24}$ alkyl (meth) acrylate and $C_{14}$ to $C_{24}$ alkyl(meth)acrylamide, with at least one hydrophilic monomer that is not identical to (meth) acrylic acid.

18. The composition of claim 17, wherein the at least one hydrophilic monomer is chosen from N-vinylpyrrolidone and hydroxyethyl (meth)acrylate.

19. The composition of claim 1, wherein the at least one first semi-crystalline polymer is derived from a monomer containing a crystallizable chain chosen from saturated $C_{14}$ to $C_{22}$ alkyl (meth)acrylates.

20. The composition of claim 1, wherein the at least one first semi-crystalline polymer has a crystallizable organic chain and/or a crystallizable block representing at least 30% of the total weight of the polymer.

21. The composition of claim 1, wherein the at least one first semi-crystalline polymer is present in an amount ranging from 0.1% to 30% by weight, relative to the total weight of the composition.

22. The composition of claim 21, wherein the at least one first semi-crystalline polymer is present in an amount ranging from 0.5% to 25% by weight, relative to the total weight of the composition.

23. The composition of claim 22, wherein the at least one first semi-crystalline polymer is present in an amount ranging from 1% to 20% by weight, relative to the total weight of the composition.

24. The composition of claim 1, wherein the at least one second film-forming polymer is chosen from free-radical polymers, polycondensates, and polymers of natural origin.

25. The composition of claim 1, wherein the at least one second film-forming polymer is chosen from vinyl polymers, polyurethanes, polyesters, and cellulose polymers.

26. The composition of claim 1, wherein the at least one second film-forming polymer is in a form of solid particles in aqueous dispersion.

27. The composition of claim 1, wherein the at least one second film-forming polymer is a polyurethane in a form of particles in an aqueous dispersion.

28. The composition of claim 1, wherein the at least one second film-forming polymer is dissolved in a liquid fatty phase.

29. The composition of claim 28, wherein the liquid fatty phase comprises at least one oil chosen from hydrocarbon-based oils, fluoro oils, and silicone oils of mineral, animal, plant and synthetic origin.

30. The composition of claim 28, wherein the liquid fatty phase comprises at least one oil that is volatile at room temperature.

31. The composition of claim 1, wherein the at least one second film-forming polymer is present in an amount ranging from 10% to 45% by weight, relative to the total weight of the composition.

32. The composition of claim 31, wherein the at least one second film-forming polymer is present in an amount ranging from 15% to 35% by weight, relative to the total weight of the composition.

33. The composition of claim 1, wherein said ratio ranges from 70:30 to 30:70.

34. The composition of claim 33, wherein said ratio ranges from 60:40 to 40:60.

35. The composition of claim 1, further comprising at least one additive chosen from thickeners, dyestuffs, preserving agents, fragrances, sunscreens, free-radical scavengers, waxes, oils, moisturizers, vitamins, proteins, plasticizers, sequestrants, ceramides, acidifying and basifying agents, and emollients.

36. The composition of claim 1, wherein said composition is in a form chosen from a mascara, an eyeliner, a product for the lips, a face powder, an eyeshadow, a foundation, a makeup product for the body, a concealer product, a product for the nails, an antisun composition, a skin coloring composition and a skincare product.

37. A process for making up or caring for a keratin material, comprising applying to said keratin material a composition according to claim 1.

38. A process for preparing a film comprising applying the composition of claim 1 to a keratinous material, wherein said film is more resistant to removal by cold water than to removal by warm water.

39. A process for removing makeup from a keratin material comprising:
   (i) applying the composition of claim 1 to said keratin material; and
   (ii) contacting the resultant keratin material after step (i) with warm water at a temperature ranging from 35° C. to 50° C.;
wherein step (ii) is optionally repeated.

40. A composition comprising, in a physiologically acceptable medium, at least one first semi-crystalline polymer having a melting point of greater than or equal to 30° C., and at least one second film-forming polymer that is capable of forming a hydrophobic film at room temperature; wherein said at least one semi-crystalline polymer does not comprise a polysaccharide backbone, wherein the at least one first semi-crystalline polymer and the at least one second film-forming polymer are present in said composition in an at least one second film-forming polymer/at least one first semi-crystalline polymer weight ratio ranging from 90:10 to 10:90.

41. A composition comprising, in a physiologically acceptable medium, at least one first semi-crystalline polymer having a melting point of greater than or equal to 30° C., and at least one second film-forming polymer that is capable of forming a hydrophobic film at room temperature; wherein said semi-crystalline polymer is not polycaprolactone, wherein the at least one first semi-crystalline polymer and the at least one second film-forming polymer are present in said composition in an at least one second film-forming polymer/at least one first semi-crystalline polymer weight ratio ranging from 90:10 to 10:90.

* * * * *